United States Patent [19]

Friedrich et al.

[11] Patent Number: 5,585,350
[45] Date of Patent: Dec. 17, 1996

[54] THROMBIN-INHIBITORY PROTEIN FROM TICKS

[75] Inventors: Thomas Friedrich, Darmstadt; Wolfgang Koerwer, Gruenstadt; Burkhard Kroeger, Limburgerhof; Siegfried Bialojan, Oftersheim, all of Germany

[73] Assignee: BASF Aktiengesellschaft, Ludwigshafen, Germany

[21] Appl. No.: 211,070

[22] PCT Filed: Sep. 23, 1992

[86] PCT No.: PCT/EP92/02198

§ 371 Date: Mar. 18, 1994

§ 102(e) Date: Mar. 18, 1994

[87] PCT Pub. No.: WO93/09231

PCT Pub. Date: May 13, 1993

[30] Foreign Application Priority Data

Oct. 31, 1991 [DE] Germany .......................... 41 36 087.7

[51] Int. Cl.$^6$ .......................... A61K 38/55; C07K 14/81; C12N 9/74
[52] U.S. Cl. .......................... 514/12; 530/350; 435/214
[58] Field of Search .......................... 514/12; 530/350

[56] References Cited

FOREIGN PATENT DOCUMENTS

0419099A1  3/1991  European Pat. Off. .
WO91/04275  4/1991  WIPO .

OTHER PUBLICATIONS

Characterization of Recombinant Tick Anticoagulant Peptide, Journal of Biological Cehmistry, vol. 265, No. 29, Oct. 15, 1990, Neeper et al.

Primary Examiner—Robert A. Wax
Assistant Examiner—Kawai Lau
Attorney, Agent, or Firm—Keil & Weinkauf

[57] ABSTRACT

A novel thrombin inhibitory protein from ticks with a molecular weight of about 26000 dalton and the partial amino acid sequences Val-Ala-Lys-Phe-Ala-X-Asn-Ser-Gly-Ser-Glu-Thr-Gly (SEQ ID NO: 8), His-Ala-Y-Phe-Glu (SEQ ID NO: 3), Arg-Val-Ser-Asp-Phe-Glu (SEQ ID NO: 4), Phe-Val-Tyr-Thr-Ile-Glu (SEQ ID NO: 6), where X and Y can be identical or different and each is a naturally occurring amino acid, is suitable for controlling diseases.

2 Claims, No Drawings

THROMBIN-INHIBITORY PROTEIN FROM TICKS

The present invention relates to a novel thrombin-inhibitory protein from ticks, and to processes for its preparation.

Thrombin inhibitors are important therapeutic substances used, for example, for the prophylaxis or treatment of thromboses or arterial reocclusions.

DE-A 39 31 839 describes a thrombin inhibitor which was isolated from the argasid tick Ornithodoros moubata. This protein has a molecular weight of about 15000 dalton, an isoelectric point at pH 4–5 and the N-terminal amino acid sequence SDYEFPPPKKXRPG (SEQ. I.D. NO.: 1)

EP-A 345 614 describes the thrombin inhibitor amblyommin which is isolated from ixodid ticks. This is a protein with a molecular weight of 20,000–30,000 dalton and an isoelectric point at from 5.05 to 5.65.

However, to date no protein with a thrombin-inhibitory effect which is suitable as a drug in terms of high activity, lack of antigenicity, long biological half-life and few side effects such as bleeding tendency has been found.

It is an object of the present invention to provide novel thrombin inhibitors which are suitable as drugs in terms of the abovementioned properties.

We have found that this object is achieved by a novel thrombin-inhibitory protein isolated from ticks.

The novel protein has the following physico-chemical properties: a molecular weight of 26000–29000 dalton was assigned to it by molecular sieve chromatography. A molecular weight of 11000±1500 dalton was determined by electrophoresis in a tricine SDS polyacrylamide gel. A molecular weight of 25700±3000 dalton was determined by Laemmli electrophoresis in an SDS polyacrylamide gel. Determination of the isoelectric point showed that it is at pH 4–5.

The protein binds specifically to a thrombin affinity column. It inhibits the biological activity of thrombin in an in vitro enzyme assay.

The protein band in a polyacrylamide gel cannot be stained with silver; it is visible only as an unstained spot on a stained background.

The amino terminus of the protein is blocked. The following partial amino-acid sequences were determined for the protein:

| | |
|---|---|
| Sequence I: | Val—Ala—Lys—Phe—Pro—Ala—(Ala)—Asn—Ser—Gly—Ser—Glu—Thr—Gly (SEQ ID NO: 2) |
| Sequence II: | His—Ala—(Cys)—Phe—Glu (SEQ ID NO: 3) |
| Sequence III: | 90% Arg—Val—Ser—Asp—Phe—Glu (SEQ ID NO: 4) |
| | 10% Phe—Ala—(Glu/His)—Lys (SEQ ID NO: 5) |
| Sequence IV: | 70% Phe—Val—Tyr—Thr—Ile—Glu (SEQ ID NO: 6) |
| | 30% Ala—Phe—Gln—Gly (SEQ ID NO: 7) |

The identification of the amino acids in parentheses is not entirely certain. Sequences III and IV are in each case mixtures of two sequences which occurred in the stated intensities.

The novel protein can be isolated from ticks of the genus Ornithodoros. To do this, the ticks are homogenized, expediently in a buffer of pH 6–9, preferably pH 7–8, using a homogenizer, preferably a mixer. The insoluble constituents are then removed, preferably by centrifugation.

The protein can be further purified from the resulting solution by adding a precipitant, preferably trichloroacetic acid, to precipitate other proteins from the solution, which are subsequently removed.

Further purification of the protein is possible by chromatographic methods, preferably ion exchange chromatography and/or affinity chromatography. Purification by thrombin affinity chromatography is particularly preferred.

The purification of the protein can be followed by a thrombin activity assay, which is expediently an optical assay in which a chromogenic substrate, for example Chromozym T, is converted by thrombin. The fractions containing the novel protein can be identified by their thrombin-inhibiting action when added to the optical assay.

Methods of genetic manipulation are particularly suitable for preparing the protein according to the invention.

To do this, a tick cDNA gene bank is set up in a conventional way. The gene coding for the protein according to the invention can be isolated from this gene bank by, for example, preparing a DNA probe whose sequence is obtained from the N-terminal amino-acid sequence described above by translation back using the genetic code. The appropriate gene can be found and isolated by hybridization with this DNA probe.

However, it is also possible to use the polymerase chain reaction (PCR) technique to prepare the corresponding gene or parts thereof. For example, the cDNA gene fragment for the protein according to the invention can be prepared by the PCR technique using a primer whose sequence has been obtained by translation back from the partial amino-acid sequences described above, and a second primer whose sequence is complementary to the 3' end of the cDNA gene fragment, preferably with the poly(dT) sequence. The corresponding gene can also be isolated by setting up a tick expression gene bank and screening it with an antibody which is directed against the protein according to the invention.

Once the appropriate gene has been isolated it can, by use of methods of genetic manipulation, be expressed in organisms, e.g. in bacteria, yeasts or eukaryotic cells, with the aid of an expression vector in a conventional way. The protein can be isolated from these recombinant host systems on the basis of the physicochemical properties described above.

The general procedure for the preparation, by genetic manipulation, of a novel protein when the partial amino-acid sequence is known is described in text books of genetic engineering, for example E. L. Winnacker, Gene und Klone, Verlag Chemie, Weinheim, 1984. The experimental conditions for the individual methods such as, for example, setting up a gene bank, hybridization, and expression of a gene are described by T. Manniatis in Molecular Cloning, Cold Spring Harbor Laboratory, 1990.

The protein according to the invention is preferably used in the form of its pharmaceutically acceptable salts.

The novel protein has anticoagulant properties. It can be used, for example, for the prophylaxis of thromboses or arterial reocclusions, for the treatment of thrombosis, for preserving blood or for extracorporeal circulation.

The invention is illustrated further by the following examples:

EXAMPLE 1

Purification of the thrombin-inhibitory protein from ticks.

A laboratory culture of the ticks, (Ornithodoros decoloratus) was maintained at 28° C. and 80% relative humidity. The ticks were fed at 14-day intervals by allowing them to suck the blood of rabbits. Ticks in all stages of development were frozen at −20° C.

200 g of ticks were homogenized with 1000 ml of 10 mM of sodium phosphate buffer, 150 mM NaCl (pH 7.5). The homogenate was centrifuged at 7000 rpm (Sorvall RC-5B, GS-3 rotor) for 15 minutes. The precipitate was discarded, and the supernatant (1300 ml) was treated with 60 ml of 50% by weight trichloroacetic acid by dropwise addition over 10 minutes.

The solution was made up to a volume of 2000 ml with distilled water and stirred for 15 minutes.

It was then centrifuged (7000 rpm for 20 minutes) and the supernatant was neutralized with sodium hydroxide solution.

The neutralized supernatant was introduced into dialysis tubes (exclusion volume 300 da) and dialyzed several times against 10 times the volume of 20 mM sodium phosphate, 150 mM NaCl, pH 8.0.

The solution was subsequently concentrated to one quarter the volume by ultrafiltration (Amicon YM5® membrane). The protein was precipitated with four times the volume of acetone (cooled to −50° C).

After the mixture had been incubated on dry ice for one hour it was centrifuged at 7000 rpm (Sorvall RC-5B, GS-3 rotor) for 20 minutes. The precipitate was collected, dried and resuspended in 10 mM sodium phosphate buffer pH 7.5 (5 g of precipitate in 40 ml of buffer).

About 45 ml of the resuspended precipitate were loaded (60 ml/h) onto a Q-SEPHAROSE® (Pharmacia) ion-exchange column (diameter 2.6 cm, height 8 cm) which had been equilibrated with 10 mM sodium phosphate buffer pH 7.5.

It was washed with 10 column volumes of equilibration buffer.

Subsequently a linear gradient from 200 ml of 10 mM sodium phosphate (pH 7.5) to 200 ml of 10 mM sodium phosphate (pH 7.5), 500 mM NaCl was applied.

Active fractions (as measured by thrombin inhibition) were collected.

The protein was eluted at about 350 mM NaCl.

The combined active fractions were loaded onto an affinity column with immobilized thrombin (diameter 1.2 cm, height 6.5 cm, volume 11.5 ml, 60 ml/h). The column was prepared as described in Example 3.

The column was equilibrated with 10 mM sodium phosphate pH 7.5. After loading of the protein solution, the column was washed with 10 column volumes of equilibration buffer until the absorption at 280 nm returned to zero.

It was then washed with 0.5 M NaCl, 10 mM sodium phosphate buffer pH 7.5 to remove non-specifically adsorbed material.

Protein specifically bound to thrombin was eluted with 0.1M glycine, 0.5M NaCl pH 2.8. The column was subsequently immediately returned to pH 7.5 with phosphate buffer.

The individual fractions were neutralized with 0.1M NaOH and examined for their thrombin-inhibitory action.

The fractions eluted with glycine/NaCl buffer pH 2.8 had a thrombin-inhibiting action.

The collected active fractions were, after neutralization, diluted with water (1:10) and loaded onto a MONO-Q® column (Pharmacia, volume 1 ml).

The column was equilibrated with 10 mM sodium phosphate buffer pH 7.5 (buffer A). It was washed with buffer A until the absorption returned to zero (10 minutes), and then a change was made in 50 minutes (flow rate 0.5 ml/min) to 10 mM sodium phosphate, pH 7.5, 500 mM NaCl (buffer B).

The thrombin-inhibiting activity was eluted at about 70% buffer B.

Thrombin-inhibiting fractions were collected.

The collected fractions were purified further on a RP 318® (Biorad) reverse-phase HPLC column. The column was equilibrated with 0.1% by weight trifluoroacetic acid (TFA) in distilled water. The combined active fractions were loaded onto the column, which was eluted with a gradient to 0.1% by weight TFA in acetonitrile at a flow rate of 1 ml/min over the course of one hour. The absorption at 280 nm was determined. 0.5 ml fractions were collected and evaporated to dryness, and the residue was taken up in phosphate-buffered saline (PBS) (0.8 g/l NaCl, 0.2 g/l HCl, 0.144 g/l sodium phosphate, 0.2 g/l potassium phosphate, pH 7.5) and the inhibitory activity was determined.

Protein was determined by the method of Bradford (Anal. Biochem., 72, (1976) 248–254) using bovine serum albumin (Boehringer Mannheim) as standard protein.

The purification of the thrombin-inhibiting protein is summarized in the table which contains the data from three independent experiments on the purification of the thrombin-inhibiting protein.

TABLE

| Table | Exper. No. | Volume [ml] | Concentration [mg/ml] | Protein [mg] | Thrombin inhibition [%] | Spec. activity [U/mg] |
|---|---|---|---|---|---|---|
| Q-SEPHAROSE® load | (1) | 20 | 0.3 | 6 | 91 | 2.7 |
|  | (2) | 50 | 0.232 | 11.6 | 66 | 2.2 |
|  | (3) | 40 | 1.23 | 49.2 | 100 | 0.8 |
| Q-SEPHAROSE eluate | (1) | 52 | 0.001 | 0.052 | 87 | 800 |
|  | (2) | 30 | 0.011 | 0.33 | 88 | 81 |
|  | (3) | 108 | 0.035 | 3.78 | 93 | 30 |
| Affinity column eluate | (1) | 7 | 0.001 | 0.007 | 45 | 300 |
|  | (2) | 35 | 0.001 | 0.035 | 60 | 450 |
|  | (3) | 34 | 0.009 | 0.306 | 90 | 90 |
| MONO-Q®-eluate | (2) | 4 | 0.01 | 0.04 | 63 | 1600 |
|  | (3) | 5 | 0.029 | 0.145 | 63 | 550 |

TEXT FOR EXAMPLES 2 AND 3

EXAMPLE 4

Determination of the molecular weight by molecular sieve chromatography

Material which had been purified by MONO-Q® chromatography was fractionated at a flow rate of 1 ml/min in 20 mM sodium phosphate, 150 mM NaCl, pH 7.5, on a type TSK® molecular sieve column (Pharmacia, Spherogel TSK 3000® SW, diameter 7.5 mm, height 60 cm).

The calibration proteins were treated in the same way (serum albumin MW 67000 da, ovalbumin MW 45000 da, chymotypsinogen A MW 25000 da).

The logarithms of the molecular weights of the calibration proteins were plotted against their elution times.

The thrombin inhibition by the eluted fractions of the sample was determined.

The logarithm of the molecular weight of the inhibitor was found by interpolation of the elution time on the calibration plot.

This determination showed that the molecular weight was from 26000 to 29000 dalton.

EXAMPLE 5

Determination of the molecular weight by tricine SDS polyacrylamide gel electrophoresis.

(Reference: Analytical Biochemistry, 166 (1987) 368–379 Tricine-Sodium Dodecyl Sulfate-Polyacrylamide Gel Electrophoresis for the Separation of Proteins in the range from 1–1000 kda, Schägger, H. and von Jagow, G.)

The gel electrophoresis was carried out as specified in the reference at 20 mA and 1400 V, 30 watt.

The molecular weight determined by this method was 11000±1500 dalton.

The calibration proteins were intact myoglobin 17.2 kda, myoglobin I+II 14.6 kda, myoglobin I 8.2 kda, myoglobin II 6.4 kda, myoglobin III 2.6 kda and myoglobin 1–14.

EXAMPLE 6

Determination of the molecular weight by SDS gel electrophoresis (reference: Nature 227, (1970) 680–685, Cleavage of structural proteins during the assembly of the head of bacteriophage T4, Lämmli, U.K.).

The gel electrophoresis was carried out as specified in the reference.

The molecular weight determined by this method was 25700±3000 dalton.

The following calibration proteins were used to determine the molecular weight:

| Phosphorylase b (rabbit muscle) | 94000 dalton |
| Bovine serum albumin | 67000 dalton |
| Ovalbumin (egg white) | 43000 dalton |
| Carbonic anhydratase (bovine erythrocytes) | 30000 dalton |
| Trypsin inhibitor (soybeans) | 20000 dalton |
| α-Lactalbumin (cow's milk) | 14400 dalton |

EXAMPLE 7

Partial sequencing of the inhibitor

The inhibitor purified as described above was blocked at the N-terminus and therefore could not be sequenced directly. It was therefore protease-cleaved into peptides. Reduction and carboxymethylation.

2.8 ml of protein solution (0.029 mg/ml) were mixed with 0.28 ml of buffer (1M tris/HCl, 0.5M guanidine hydrochloride, pH 8.6). Then 0.116 ml of dithiothreitol (DTT, 10 mg/ml) was added and the mixture was incubated at 37° C. for 10 minutes. Then, after addition of 0.185 ml of iodoacetamide (10 mg/ml), the mixture was incubated at 37° C. for 90 minutes. The reaction was stopped with 0.073 ml of DTT as above.

The protein treated in this way was cleaved with trypsin at 37° C. overnight. The protease was employed in a ratio of from 1:10 to 1:100 (weight of protease:weight of protein). The protease was dissolved as specified by the manufacturer.

The peptide mixture was subjected to reverse phase HPLC on RP 318®. The mixture was adjusted to a final concentration of 0.1% by weight trifluoroacetic acid (TFA) and loaded into a Hewlett Packard HPLC system (HP 1090 liquid chromatograph). Washing with solvent A (0.1% by weight TFA in $H_2O$) was carried out for 5 minutes and then the content of solvent B (90% by volume acetonitrile, 10% by volume $H_2O$, 0.1% by weight TFA) was increased to 50% over the course of 120 minutes. The absorption of the eluate at 214 and 280 nm was measured. Absorbing fractions were collected. The peptides were sequenced in an Applied Biosystems 477 A protein sequencer in accordance with the manufacturer's instructions.

The following sequences were obtained:

| Sequence I: | Val—Ala—Lys—Phe—Pro—Ala—(Ala)—Asn—Ser—Gly—Ser—Glu—Thr—Gly (SEQ ID NO: 2) |
| Sequence II: | His—Ala—(Cys)—Phe—Glu (SEQ ID NO: 3) |
| Sequence III: | 90% Arg—Val—Ser—Asp—Phe—Glu (SEQ ID NO: 4) |
| | 10% Phe—Ala—(Glu/His)—Lys (SEQ ID NO: 5) |
| Sequence IV: | 70% Phe—Val—Tyr—Thr—Ile—Glu (SEQ ID NO: 6) |
| | 30% Ala—Phe—Gln—Gly (SEQ ID NO: 7) |

The identification of the amino acids in parentheses is not entirely certain. Sequences III and IV are each mixtures of two sequences which occurred to the stated extents.

EXAMPLE 8

Determination of the isoelectric point by isoelectric focusing

A determination was carried out with an LKB Multiphor 2117 (horizontal system) and an LKB 2103 power supply. Precast gels were employed (Pharmacia Ampholine PAG-plate pH 3.5–9.5). The standard proteins used were amyloglycosidase pH 3.5, soybean trypsin inhibitor pH 4.55, β-lactoglobulin A pH 5.2, bovine carbonic anhydrase pH 5.85, human carbonic anhydrase pH 6.55, horse myoglobin pH 6.85 and 7.35, lentil lectin pH 8.15, 8.45 and 8.65 and trypsinogen pH 9.3.

Focusing conditions: 1500 volt, 30 watt.

Buffers: Anode 1M phosphoric acid

Cathode: 1M sodium hydroxide solution

The plates were prefocussed for 30 minutes to form a pH gradient. The samples were applied to filter disks which were placed on the gel. Focusing was continued for 30 minutes, the filter disks were removed, and the focussing was terminated after a further 30 minutes. The gels were immediately cut into 2 mm slices and transferred into distilled water. The protein was eluted from the gel slices overnight. The position of the thrombin inhibitor was determined by a thrombin inhibition assay. The pH can also be determined directly by a pH electrode. Hirudin was used for comparison and had an isoelectric point of pH 3.5 and below. The novel inhibitor had an isoelectric point at pH 4–5.

We claim:

1. An isolated and purified protein with a thrombin-inhibitory effect from ticks of the genus Ornithodoros, having an isoelectric point at pH 4–5, a molecular weight of 25700±3000 dalton determined by SDS polyacrylamide gel electrophoresis by the Laemmli method, and the partial amino acid sequences Val-Ala-Lys-Phe-Ala-Xaa-Asn-Ser-Gly-Ser-Glu-Thr-Gly (SEQ ID NO: 8), His-Ala-X22-Phe-Glu (SEQ ID NO: 3), Arg-Val-Ser-Asp-Phe-Glu (SEQ ID NO: 4), Phe-Val-Tyr-Thr-Ile-Glu (SEQ ID NO: 6), where X22 can be identical or different and each is a naturally occurring amino acid.

2. A method of inhibiting thrombin using the protein of claim 1.

* * * * *

UNITED STATES PATENT AND TRADEMARK OFFICE
CERTIFICATE OF CORRECTION

PATENT NO.: 5,585,350

DATED: December 17, 1996

INVENTOR(S): FRIEDRICH et al.

It is certified that error appears in the above-identified patent and that said Letters Patent is hereby corrected as shown below:

Column 9, claim 1, line 6, "Val-Ala-Lys-Phe-Ala-Xaa-Asn-Ser-" should read -- Val-Ala-Lys-Phe-Pro-Ala-Xaa-Asn-Ser --.

Column 9, claim 1, line 7, "X22" should be --Xaa--.

Column 10, claim 1, penultimate line, "X22" should be --Xaa--.

Signed and Sealed this

First Day of April, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
( A ) LENGTH: 14 amino acids
( B ) TYPE: amino acid
( D ) TOPOLOGY: linear ( x i ) SEQUENCE DESCRIPTION: SEQ ID NO: 1:

Ser Asp Tyr Glu Phe Pro Pro Pro Lys Lys Xaa Arg Pro Gly
 1               5                   10

( 2 ) INFORMATION FOR SEQ ID NO: 2:

( i ) SEQUENCE CHARACTERISTICS:
( A ) LENGTH: 14 amino acids
( B ) TYPE: amino acid
( D ) TOPOLOGY: linear ( x i ) SEQUENCE DESCRIPTION: SEQ ID NO: 2:

Val Ala Lys Phe Pro Ala Xaa Asn Ser Gly Ser Glu Thr Gly
 1               5                   10

( 2 ) INFORMATION FOR SEQ ID NO: 3:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO: 3:

His Ala Xaa Phe Glu
 1               5

( 2 ) INFORMATION FOR SEQ ID NO: 4:

( i ) SEQUENCE CHARACTERISTICS:
( A ) LENGTH: 6 amino acids
( B ) TYPE: amino acid
( D ) TOPOLOGY: linear ( x i ) SEQUENCE DESCRIPTION: SEQ ID NO: 4:

Arg Val Ser Asp Phe Glu
 1               5

( 2 ) INFORMATION FOR SEQ ID NO: 5:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO: 5:

Phe Ala Xaa Lys
 1

( 2 ) INFORMATION FOR SEQ ID NO:6:

( i ) SEQUENCE CHARACTERISTICS:
( A ) LENGTH: 6 amino acids
( B ) TYPE: amino acid
( D ) TOPOLOGY: linear ( x i ) SEQUENCE DESCRIPTION: SEQ ID NO: 6:

Phe Val Tyr Thr Ile Glu
 1               5

( 2 ) INFORMATION FOR SEQ ID NO: 7:

( i ) SEQUENCE CHARACTERISTICS:
  ( A ) LENGTH: 4 amino acids
  ( B ) TYPE: amino acid
  ( D ) TOPOLOGY: linear ( x i ) SEQUENCE DESCRIPTION: SEQ ID NO: 7:

Ala Phe Gln Gly
 1

( 2 ) INFORMATION FOR SEQ ID NO: 8:

( i ) SEQUENCE CHARACTERISTICS:
  ( A ) LENGTH: 13 amino acids
  ( B ) TYPE: amino acid
  ( D ) TOPOLOGY: linear ( x i ) SEQUENCE DESCRIPTION: SEQ ID NO: 8:

Val Ala Lys Phe Ala Xaa Asn Ser Gly Ser Glu Thr Gly
 1               5                   10